United States Patent [19]

Roffia et al.

[11] Patent Number: 4,918,194

[45] Date of Patent: Apr. 17, 1990

[54] PROCESS FOR THE SYNTHESIS OF A N,N-DIALKYL-HYDROXYLAMINE

[75] Inventors: Paolo Roffia, Saronno; Sergio Tonti, Mestre; Alberto Cesana, Carate Brianza; Maria Angela Mantegazza, Cambiago; Mario Padovan, Milan, all of Italy

[73] Assignee: Montedipe S.p.A., Milan, Italy

[21] Appl. No.: 262,354

[22] Filed: Oct. 25, 1988

[30] Foreign Application Priority Data

Oct. 29, 1987 [IT] Italy .................. 22452 A/87

[51] Int. Cl.$^4$ ............... C07D 295/22; C07C 87/02
[52] U.S. Cl. ............................. 546/184; 548/542; 564/300; 564/301
[58] Field of Search ............... 564/300, 301; 546/184; 548/400, 542

[56] References Cited

U.S. PATENT DOCUMENTS 2,169,976 8/1939 Guenther et al. .............. 564/301
4,410,501 10/1983 Taramasso et al. ............ 502/202

FOREIGN PATENT DOCUMENTS 0779239 7/1957 United Kingdom ............ 564/300

*Primary Examiner*—Richard L. Raymond
*Assistant Examiner*—Peter G. O'Sullivan
*Attorney, Agent, or Firm*—Stevens, Davis, Miller & Mosher

[57] ABSTRACT

The invention relates to a process for the synthesis of an N,N-dialkyl-hydroxylamine by reaction of the corresponding dialkylamine with $H_2O_2$, said reaction being carried out in the presence of a catalyst based on titanium-silicalite.

6 Claims, No Drawings

PROCESS FOR THE SYNTHESIS OF A N,N-DIALKYL-HYDROXYLAMINE

BACKGROUND OF THE INVENTION

Several methods are already known for synthesizing a N,N-dialkyl-hydroxylamine; in particular nitrones can be reduced either to disubstituted hydroxylamines by means of lithium aluminum hydride or by means of potassium boro-hydride or by hydrogenation on platinum black [Coll. Czech. Chem. Comm. 20, 202 (1955), JACS 79, 5739 (1957); 78, 6208 (1956); Gazz. Chim. Ital. 51, II, 306 (1921)]. The pyrolysis of trialkylamine oxides, known the Cope reaction, is useful for the synthesis of N,N-dialkyl-hydroxylamines as well.

Should the amine oxide have more than one alkyl group capable of forming an olefin, a mixture of hydroxylamines is obtained [Org. Synthesis Coll. Vol. IV; 612 (1963)].

The N,N-dialkyl-hydroxylamines may also be prepared either by reaction of compounds containing an N-O bond, by letting said compounds react with organometallic compounds [J. Chem. Soc. 119, 251 (1921)] or by alkylation of hydroxylamines or N-alkyl-hydroxylamines with alkyl halogenides [J. Org. Chem. 28, 1068 (1963); U.S. Pat. No. 3,491,151; C.A. 72, 132,130f (1970)]. It is also known that secondary amines, when treated with hydrogen peroxide or with acylperoxides, give rise to N,N-dialkyl-hydroxylamines |Chem. Ber. 65, 1799 (1932); Arch. Pharm. 299, 166 (1966); JACS 72, 2280 (1950); J. Chem. Soc. 3144 (1963)|. The reaction is of a general type and can be used with primary amines as well. The modalities followed till now proved to be, however, extremely unsatisfactory, owing to the low yield in the desired product. Moreover the oxidation of the carbon atoms in alpha position, with respect to nitrogen, gave rise to a complex mixture of products. The oxidation of secondary amines with hydrogen peroxide was carried out in the presence of a reaction promoter as well, in particular in the presence of an ester of formic acid (German Patent No. 1.004.191) or in the presence of a usual catalyst, containing Mo, W and the like (Belgian patent No. 615,736). In any case the yields are low, whereas the reaction of decomposition of hydrogen peroxide clearly prevails over the reaction giving rise to hydroxylamine. Also the above mentioned preparation processes of N,N-dialkylamines, which are not based on oxidation by means of hydrogen peroxide-therefor, are characterized by use of expensive reactants, by the handling of rather unstable compounds, by formation of a large number of by-products, and by difficulty in separating the useful product.

It has now, surprisingly, been found that the preparation of N,N-dialkylhydroxylamine (in particular of N,N-diethyl-hydroxylamine) can be very much improved by carrying out the oxidation of the corresponding amine by means of hydrogen peroxide in the presence of a particular catalyst.

DISCLOSURE OF THE INVENTION

The invention resides in a process for the synthesis of N,N-dialkyl-hydroxylamine having formula:

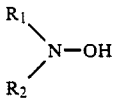

(I)

wherein $R_1$ and $R_2$, which may be the same or different, represent an alkyl, cycloalkyl, alkyl-cycloalkyl or cycloalkyl-alkyl group, having from 1 to 40 C atoms, or they are part of a cycloaliphatic ring, containing a hetero-atom N and having from 1 to 8 C atoms, by reaction with hydrogen peroxide of the corresponding (secondary) dialkyl-amine having formula:

(II)

characterized in that the reaction is carried out in the presence of a catalyst based on titanium-silicalite. The term "titanium-silicalite" is defined in European patent application 88/111,138 and in European patent No. 267362.

Extraordinary results were obtained starting from secondary amines in which $R_1$ and $R_2$ contained from 1 to 8 C atoms, or from heterocyclic compounds of pyrrolidinic or piperidinic nature. In particular we cite diethyl-amine; dipropyl-amine; dioctylamine; N-methyl,N-ethyl-amine and pyrrolidine.

The practical interest of these hydroxylamine compounds comes from their use in different fields as reduction agents, stabilization agents or polymerization inhibitors.

In particular, on account of these specific properties, these compounds are satisfactorily used, replaciing the hydrazine derivatives as deoxygenating agents of the waters to be fed into thermal plants or in general into steam generating plants. By the process according to the invention, one obtains a high yield with respect to hydrogen peroxide (generally between 85 and 95%), high selectivity with respect to the starting amine (higher than 90 and even than 95%), and practically a quantitative conversion of the starting amine.

The hydroxylation of the secondary amine by means of $H_2O_2$ may be carried out in different ways; for instance, we may operate, either in the absence or in the presence of a solvent, said solvent being, for instance, water or a suitable organic compound miscible with water, such as the aliphatic alcohols, or mixtures thereof. Good results were obtained by using as solvent a tertiary alcohol which is practically inert with respect to the oxidizing system. Really extraordinary results were obtained by using t-butyl or t-amyl alcohol. The temperatures range generally between 25° and 150° C., preferably between 40° and 120° C. The hydroxylation reaction of the dialkylamines may be generally carried out at atmospheric pressure or (preferably at a pressure higher than atmospheric to keep both solvent and reactants in the liquid phase. The catalyst is used preferably in a form finely diespersed in the reaction medium, in amounts ranging from 0.1 to 50 parts by weight (preferably from 1 to 30 parts) per 100 parts of dialkylamine. The weight ratio between dialkylamine and solvent ranges generally from 1 to 30 parts, and preferably from 1 to 20 parts, by weight of amine per 100 parts of solvent. The reaction stoichiometry requires an amount of hydrogen peroxide equivalent to the amine amount. Applicants may generally operate according to a molar ratio between the two reactants (hydrogen peroxide:-dialkylamine) ranging from 0.9 to 1.2, and preferably from 0.9 to 1.1.

The process according to the invention may be carried out either in a semicontinuous way (by feeding continuously hydrogen peroxide only) or in a continuous way (by feeding continuously both the reactants). The reaction effluent consists of a suspension that has to be filtered to recover the catalyst (which is recycled to the reaction). If the filter is placed inside the reactor, the recovered effluent consists of a solution of the starting amine, of the reaction product, of the reaction water, and of the solvent. The different components can be recovered from this solution by known methods (distillation, crystallization, extraction, and the like). Non-converted reactants and solvent are recycled to the hydroxylation reaction, whereas the reaction product is recovered and subjected to other optional purification operations, according to the desired quality.

The following examples will illustrate the invention, without limiting, however, its scope.

EXAMPLE 1

A glass reactor equipped with a stirrer and heating jacket was pressurized with nitrogen, after having obtained a vacuum within by means of a mechanical pump the reactor was loaded with 1.5 g of a finely subdivided powder, obtained by grinding a titanium silicalite (prepared according to example 2 of European patent No. 267362), with 7.21 g of diethylamine and with 50 cm$^3$ of t-butyl alcohol. The temperature was gradually increased, by feeding a thermostatic liquid at a temperature of 80° C. into the reactor jacket. At this point hydrogen peroxide (as an aqueous solution at 30% by weight) was added. The addition was carried on over 35 minutes, by feeding on the whole 5.97 g of dilute $H_2O_2$, corresponding to 0.056 moles of pure $H_2O_2$. Afterwards the solution was cooled and directly analysed. The non-converted diethylamine accounted for 3.49 g, whereas the formed N,N-diethylhydroxylamine was 4.32 g, which corresponds to a 51.5% conversion, with a 95.5% selectivity to N,N-diethyl-hydroxylamine. The hydrogen peroxide conversion was practically complete, with a yield of N,N-diethyl-hydroxylamine of 87.1%.

EXAMPLE 2

Example 1 was repeated but increasing the hydrogen peroxide amount to 9.63 g, corresponding to 0.090 moles, and by carrying out the addition over 54 minutes. The obtained results were as follows:
diethylamine conversion 80.4%
amine selectivity to N,N-diethyl-hydroxylamine 92.3%
N,N-diethyl-hydroxylamine yield (with respect to $H_2O_2$) 80.9%
hydrogen peroxide conversion 99.8%

EXAMPLE 3

Example 2 was repeated but increasing the t-butanol amount to 100 cm$^3$ and keeping unaltered the other reactants and the reaction conditions. The obtained results were as follows:
diethylamine conversion 84.5%
amine selectivity to N,N-diethyl-hydroxylamine 88.7%
N,N-diethyl-hydroxylamine yield (with respect to $H_2O_2$) 78.3%
hydrogen peroxide conversion 99.4%

EXAMPLE 4

Example 1 was repeated by adding 25 cm$^3$ of $H_2O_2$ and 25 cm$^3$ of t-butanol (as the dispersing medium for the catalyst) and changing the reaction temperature to 60° C. The obtained results were as follows:
diethylamine conversion 40.9%
amine selectivity to N,N-diethyl-hydroxylamine 54.2%
N,N-diethyl-hydroxylamine yield (with respect to $H_2O_2$) 41.1%
$H_2O_2$ conversion 91.6%

EXAMPLE 5 (COMPARATIVE EXAMPLE)

Example 1 was repeated, omitting the addition of the catalyst. The obtained results were very poor and were as follows:
diethylamine conversion 23.4%
selectivity to N,N-diethyl-hydroxylamine 17.3%
N,N-diethyl-hydroxylamine yield (with respect to $H_2O_2$) 7.2%
hydrogen peroxide conversion 66.9%

EXAMPLE 6

7.4 g of pyrrolidine, 50 cm$^3$ of t-butyl alcohol and 1.5 g of the same (finely subdivided)titanium-silicalite were loaded into the apparatus described in example 1. The suspension, kept under stirring by means of a magnetic stirrer, was heated at 80° C.; afterwards, one started feeding dilute hydrogen peroxide (at 30% by weight) by means of a metering pump. The addition went for over 150 minutes, with an overall addition of 0.054 moles of $H_2O_2$. When the addition was over, the solution was cooled and analysed. The obtained results were as follows:
pyrrolidine conversion 30.5%
pyrrolidine selectivity to N-hydroxy-pyrrolidine 30.4%
N-hydroxy-pyrrolidine yield (with respect to $H_2O_2$) 18.0%
hydrogen peroxide conversion 99.7%

EXAMPLE 7 (COMPARATIVE EXAMPLE)

Example 6 was repeated without using any catalyst. The results obtained were very poor and were as follows:
pyrrolidine conversion 25.4%
pyrrolidine selectivity to N-hydroxy-pyrrolidine 0.2%
N-hydroxy-pyrrolidine yield (with respect to $H_2O_2$) 0.1%
hydrogen peroxide conversion 93.6%

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:
1. A process for the synthesis of N,N-dialkylhydroxylamine having the formula (I):

wherein $R_1$ and $R_2$, which may be the same or different, represent an alkyl, cycloalkyl, alkyl-cycloalkyl or cycloalkyl-alkyl group, having from 1 to 40 C atoms, or they are part of a cycloaliphatic ring, containing a hetero-atom N and having from 4 to 8 C atoms, by reaction with hydrogen peroxide of the corresponding (secondary) dialkyl-amine having formula (II):

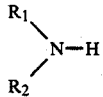 (II)

wherein $R_1$ and $R_2$ are as defined above; comprising carrying out said reaction in the presence of a catalyst based on titanium-silicalite.

2. A process according to claim 1, wherein said secondary amine contains alkyl groups having from 1 to 8 C atoms or is a heterocyclic compound of pyrrolidinic or piperidinic nature.

3. A process according to claim 2, wherein said amine is selected from the group consisting of dimethylamine; diethylamine; N-methyl,N-ethyl-amine, dipropylamine; dioctylamine and pyrrolidine.

4. A process according to claim 1, wherein said reaction is carried out in a solvent selected from the group consisting of water, aliphatic alcohols and mixtures thereof, according to an amine:solvent weight ratio between 1:100 and 30:100, the reaction temperature ranging from 25° to 150° C.

5. A process according to claim 1, wherein the catalyst amount ranges from 0.1 to 50 parts by weight per 100 parts of amine.

6. A process according to claim 1, wherein the $H_2O_2$:amine molar ratio ranges from 0.9 to 1.2.

* * * * *